(12) United States Patent
Kanitz et al.

(10) Patent No.: US 7,364,387 B2
(45) Date of Patent: Apr. 29, 2008

(54) METHOD AND DEVICE FOR ACCELERATING THE DECOMPOSITION OF BIOGENIC ORGANIC MATTER IN REFUSE DISPOSAL SITES

(75) Inventors: Jürgen Kanitz, Bochum (DE); Jürgen Forsting, Münster (DE)

(73) Assignees: A3-Abfall-Abwasser-Anlagentechnik GmbH, Gelsenkirchen (DE); Stadtreninigung Hamburg, Hamburg (DE)

( * ) Notice: Subject to any disclaimer, the term of this patent is extended or adjusted under 35 U.S.C. 154(b) by 485 days.

(21) Appl. No.: 10/480,860

(22) PCT Filed: Jun. 26, 2002

(86) PCT No.: PCT/DE02/02331

§ 371 (c)(1),
(2), (4) Date: Dec. 12, 2003

(87) PCT Pub. No.: WO03/004182

PCT Pub. Date: Jan. 16, 2003

(65) Prior Publication Data

US 2004/0175819 A1    Sep. 9, 2004

(30) Foreign Application Priority Data

Jun. 29, 2001  (DE) ................ 101 31 026

(51) Int. Cl.
*B09B 1/00* (2006.01)
(52) U.S. Cl. .................... 405/129.2; 405/129.3
(58) Field of Classification Search ............. 405/129.2, 405/128.2, 128.25, 128.3
See application file for complete search history.

(56) References Cited

U.S. PATENT DOCUMENTS

| 4,837,153 A | 6/1989 | Laurenson, Jr. |
| 5,632,798 A | 5/1997 | Funk et al. |
| 6,024,513 A | 2/2000 | Hudgins et al. |

*Primary Examiner*—John Kreck
(74) *Attorney, Agent, or Firm*—Jonathan Myers; Andrew Wilford

(57) ABSTRACT

The invention relates to a method and device for accelerating the decomposition of biogenic organic matter in refuse disposal sites. According to the method, at least one suction line is inserted into a disposal site debris heap (11) via which the arising refuse site gases are removed by suction. According to the invention, the quantity of gas removed by suction in the area of the bottom of the refuse disposal site should be greater than the quantity of gas arising in this area due to decomposition whereby enabling oxygen from the outside air to penetrate into the debris heap and transforming the decomposition process into an, at least to a large extent, aerobic decomposition.

Figure 1:
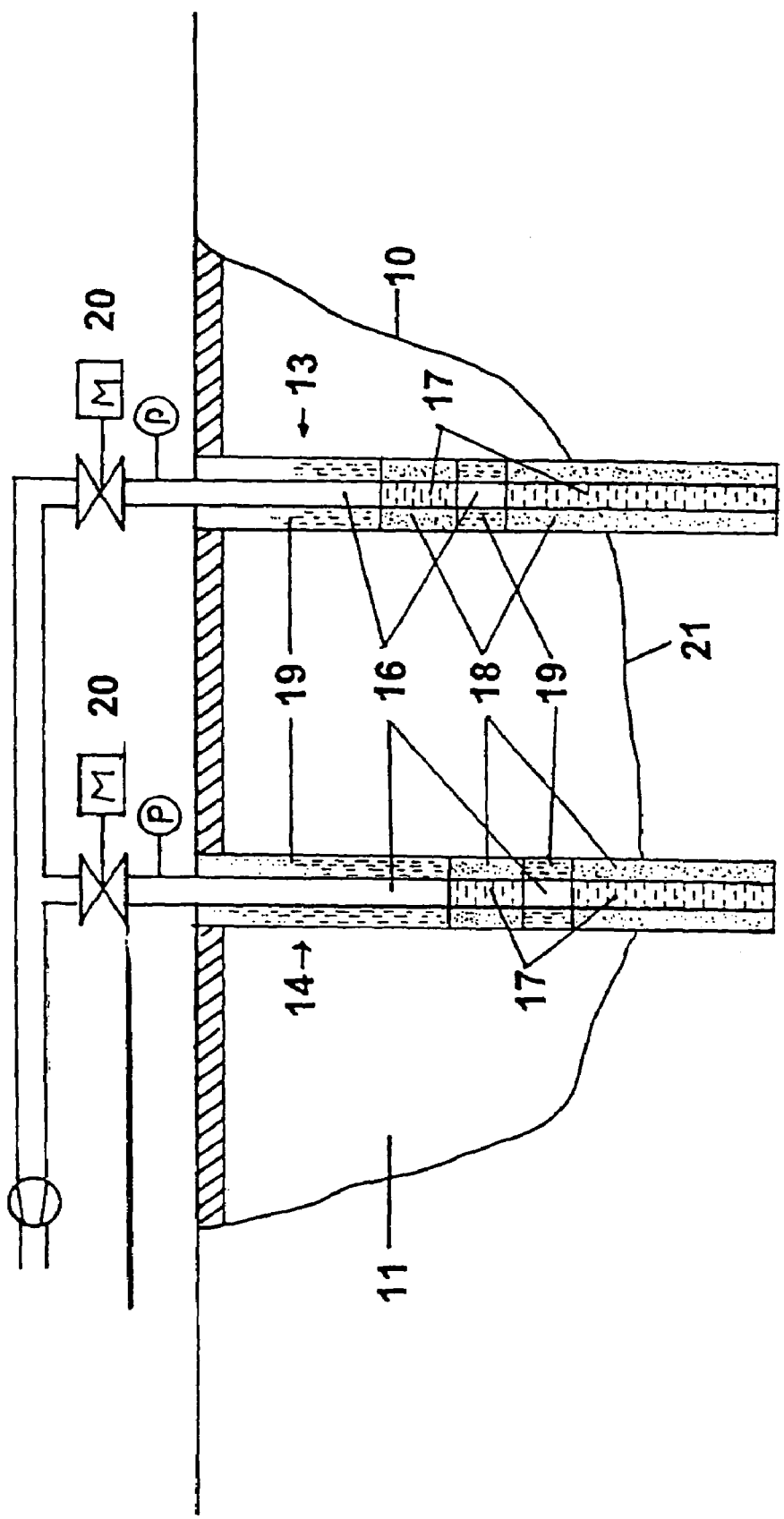

13 Claims, 2 Drawing Sheets

METHOD AND DEVICE FOR ACCELERATING THE DECOMPOSITION OF BIOGENIC ORGANIC MATTER IN REFUSE DISPOSAL SITES

The invention relates to a method of accelerating the decomposition of biogenic organics in garbage dumps in which the refuse is layered upon a disposal site ground and is stored in a heap in which a suction pipe is incorporated by which the gases produced by the garbage in the heap can be drawn off.

The invention relates further to a device for carrying out the aforementioned method with at least one suction pipe incorporated in the heap or pile and which extends to the ground region of the dump, at least one measurement sensor for analyzing and measuring the concentration of the gases arising in the heap or pile and a control device for adjusting the suction power, namely, the through-flow quantity of the drawn off gases in the suction pipe or suction pipes in dependence upon the gas or gases detected by the measurement sensor and their concentration.

By garbage or refuse here such mixtures will be understood as arise as household waste or household wastes similar to commercial waste and which aside from nondecomposible inorganic components have organic components which in the presence of oxygen and sufficient moisture decompose aerobically and in the absence of oxygen decompose anaerobically. Earlier methods to ensure the greatest possible protection of the environment in waste disposal, by garbage separation conditions were provided for aerobic composting or anaerobic sewage treatment in columns or the like to allow the value of the waste to be recovered without continuously burdening dump sites. Consequently aerobically decomposed organic waste can be used as compost. In an anaerobic waste treatment, the recovered methane can be used as valuable energy. Correspondingly, it is also possible to dry the waste to the extent that it will be sufficiently stable for use as a fuel to recover the fuel value.

Especially in earlier years, the waste that was collected was layered in refuse dumps or dumped into previously provided or naturally occurring burial sites. After filling the capacity of these sites and their closure, the dumps or heaps were more or less covered and in certain cases even planted. The decomposition of organic components occurring over time in the covered piles or heaps, however, could reach intolerable concentrations especially in locations close to municipalities or within municipalities.

In such closed dumps, therefore, suction pipes were introduced through which the dump gases which were produced could be evacuated. The starting high methane concentrations of up to 60 volume percent were economically evacuated and the methane burned in power plants. With time however, the decomposition process slows so that the percentage methane gas content in the evacuated dump gases becomes significantly less so that finally concentrations are reached which exclude economically combustion on the one hand but on the other hand still reach values of for example up to 25 volume percent which create the danger of explosions in closed spaces. By gas migration, large distances (up to 300 meters have been found) can be bridged before the gas emerges for example in cellars or sewage shafts and there forms dangerous explosive gas mixtures.

To minimize these dangers, according to the state of the art, the evacuation of dump gasses is carried out for several hours. For this purpose, the gas pipes, well points or the like must be distributed over the entire height of the heap or pile to allow the dump gases to be evacuated and the suction power must be correspondingly matched to the quantities of the dump gases which are produced.

When the $CH_4$ concentration drops below about 25 to 27 volume percent, the combustability of the gas terminates. Either the $CH_4$ composition must be raised above 30 volume percent by means of the admixture of gas therewith to form a combustible gas mixture or the gas mixture must without the additional mixing of gas therewith be oxidized in a catalyzer stage to $CO_2$.

Based upon the usual configuration of gas wells with sufficient filtering up to the surface of the heap, a strong suction can be effected only in the region of the surface and thus there is an aeration of the heap only close to the surface and a conversion of the biogenic organics in this region. In deeper layers which form, in the greater part of the pile there is no change in the conversion conditions.

Through the biological decomposition on the other hand, as a result of hydrolysis processes, organic compounds tend to be transformed into a water soluble form and can be carried away by the percolating water. This gives rise to the possibility of ground water loading (measured as biological oxygen demand (BOD) and $NH_4$ content in the percolating water. Based upon present understandings, the danger of gas emissions and percolating water emissions can last between 50 and 100 years.

It is therefore the object of the present invention to provide a method and a device of the type described at the outset which can achieve a minimization of the operating cost in a garbage dump by a massively accelerating decomposition of the biogenic organics in the dump. The duration of quasicomplete decomposition of the biologically decomposable organics should be significantly reduced as a rule to less than 10 years.

The core concept of the present invention resides in that aerobic conditions are created in the heap or pile under which the biological decomposition process is carried out substantially more quickly than anaerobic conditions. By the feature that, in the region of the ground beneath the dump the gas quantity which is sucked out is greater than the gas quantity produced in this region by decomposition and is as a function of the suction power after some time capable of establishing a forced aerobic condition in the pile.

Through the cover of the dump, oxygen is sucked with the external air into the dump. By contrast with the suction devices known from the state of the art, the suction is effected in the lower portion of the dump, preferably in the lower third, that is preferably in a zone which is in general up to a height of a maximum of 6 meters above the ground on which the dump rests in a gas-filled region. The suction should in any case be effected close to the base and as far as possible not above the bottom region which has here been described. The height of the suction zone depends however also upon the height of the layered pile or heap. The dump is subjected to oversuction when the suction level in the central region of the dump is so established that by means of the suction applied to the dump, an approximately constant subatmospheric pressure is applied thereto. The dump is so oversuctioned that the flow velocity in the dump from the suction point to the outer regions of the dump at which the ambient air flows into the latter, falls strongly. Because of the reduced flow velocity in large areas, a local overheating does not occur, there is a formation of shrinkage cracks and other passages through which the air preferably flows into the dump.

Local overheating is the case when, according to the methods known from the state of the art, air was forced into the dump through lances or gas wells. At the entry location in a comparatively small volume of the dump, there was the greatest flow with a high oxygen level. That resulted in an intensive local biological and chemical conversion of the biogenic organics. That gave rise in inlet regions to local overheating partly leading to local combustion nests. Because of the temperature increase the gas which is produced picks up a great deal more moisture than is introduced by the cold air injected into the dump. The dump is partially dried out, thereby retarding further biological transformation. As a result of the drying out, additional shrinkage cracks arise and the result is an uncontrolled outflow of the injected air in spite of intensive aeration. Basically it is also possible via the lances introduced into the heap or pile to blow normal air or oxygen enriched air into the pile. However, such a process is not only significantly more expensive but aside from the aforedescribed problems, is also more expensive from the measurement of process control points of view.

According to the invention, the uniform aeration of the entire pile or heap results in an oxygen excess which affects an aerobic conversion whose gaseous end product is $CO_2$ and $H_2O$. It is also important that the evacuation of the gas takes places deep within the heap or pile at the ground supporting the dump and preferably in the lower third of the dump since otherwise the danger arises that the entire quantity of air drawn through the upper layers of the dump pile will be drawn off and thus pass through the suction slits after traversing only a small part of the dump volume, thereby permitting the aerobization and decomposition only in the upper region while the lower zones to the foot of the dump remain subject to aerobic decomposition without change. With the aerobization according to the invention, on the one hand by establishment of aerobic conditions, methane formation is reduced while on the other hand, aerobic transformation to $CO_2$ is greatly increased. A high $CO_2$ concentration with low methane and also low oxygen concentrations is a measurable indicator for a good aerobization if at the starting stages.

The method according to the invention allows previously practiced features to be combined with methane gas recovery in that when initially the suction pipes or well points provided are used to pump out the gases formed in the pump in the lowest region, preferably the lowest third with the correspondingly high methane content until the methane content in the gas sinks to a value below which an economical utilization of methane, for example by combustion in a thermal power plant is no longer possible.

To the extent that measurement sensors (filter cartridges) are provided at different levels in gas wells (multilevel wells) but outside the pipes incorporated in the pump, these filter cartridges can be arranged in a filter cartridge bed. Between these filter cartridge beds or the filter cartridges, clay blocks are provided to ensure that the dump gas development can be controlled by gas sampling by the measurement sensors at the different heights within the dump.

The dump gas development and their compositions indicates whether the desired suction power is sufficiently strong to ensure satisfactory aeration of the dump heap or pile over the entire volume.

According to a further feature of the invention, the gas evacuation is effected exclusively in the region of the bottom of the pump, preferably in the lower third of the pile or heap and/or preferably in the region at most six meters above the floor of the dump in a zone forming a gas-filled region (unsaturated region). At least above the previously defined zone there should be no gas evacuation although there may be small gas samplings over filter cartridges to enable the gas composition to be explored as a function of the pile or heap height so that the suctioning power may be correspondingly raised or lowered in the dump region therebelow.

Preferably the gas evacuation is carried out in the region of the floor of the dump at a multiplicity of locations which are preferably equidistant from one another. In this manner, one takes into consideration the fact that the dump extends over a large area so that a corresponding number of suction pipes or wells are advantageous.

As has already been indicated by example, a so-called multilevel well can be used at which the gas composition at different heights in the pile or heap can be measured at different locations, the measurements evaluated and the suction power so controlled as a function thereof so that at each location in the pile or heap an oxygen content is established as will be necessary for an aerobic decomposition. If one uses multiple wells or separate suction pipes, the throughflow volumes can be individually varied in each suction pipe or in each well for the dump gas which is sucked out in order to aerate more strongly regions which might still be undergoing aerobic decomposition and to optimize the aerobic decomposition.

The described method is carried out by the apparatus which, according to the invention, is characterized in that the suction opening of the suction pipe or pipes are located in the region of the floor of the dump, preferably in a region which is in the lower third of the pile or heap or in a region which is at most 6 meters from the floor of the floor of the dump. Preferably a plurality, especially mutually equidistant suction pipes are distributed in the heap or pile. In accordance with a further feature of the invention a multiplicity of suction pipes are so installed that their positions, spacings and suction power are so selected that their effective suction regions at least bound one another and preferably slightly overlap. Especially the suction power in each suction pipe should be individually controllable, preferably as a function of the measured gas concentration at their respective effective regions. The suction pipes have in their upper regions (in which no dump gases should be evacuated) a gas-tight shell as well as a clay block lying outwardly to prevent gas short circuits parallel to the unslit regions of the suction pipe.

The present invention is described in detail in connection with an example. The drawing shows FIG. 1 a cross section through a buried dump and FIG. 2 a partial cross section through a multilevel well.

According to FIG. 1, in a buried dump 10 containing refuse forming a pile or heap (11) in layers and covered at the top by a natural covering (12) for example in the form of planted soil, in the illustrated embodiment two bores (13) and (14) are provided in which respective tubes 16 with closed walls are introduced. In the present case, in addition, two filter tubes (17) are provided around which a gas-permeable gravel bed (18) is arranged. Thereover or between them are earthenware blocks (19) which prevent the gas from passing along the solid pipe or through the filter gravel layers and being drawn into the suction wells and thereby reduce the effectivity of the suction wells or suction regions. In the illustrated case, only through the gravel filters and the corresponding solid wall pipes (16) and (17) can the gas be pumped out by a motor-driven pump (20). In order to ensure that the gas is drawn out close to the base of the dump, only lower filters below the clay pipes are effective to draw the gas out of the system. This can also be realized by including a liner for the upper filter stretches.

According to a further configuration of the invention, the liner can also be height adjustable (FIG. 1). This has the advantage that an upper filter (18) can be shut off so that the suction develops further in the depth of the heap or pile.

Finally, the well can extend downwardly until below the ground water level so that via corresponding additional suction pipes or pressure pumps, ground water samples can be withdrawn.

Both wells (13) and (14) extend to a point below the floor of the dump and can terminate below the ground water level so that by appropriate pumping, water samples can be removed.

Preferably over the entire area of the dump which can extend for a number of hectares, wells (13), (14) or suction pipes can be uniformly distributed and connected with a single suction apparatus or with a multiplicity of suction apparatuses. The suction power of the entire apparatus can be controlled by suction motors operated by controllable frequency converters.

Through individual regulation of the suction power or valves provided in each suction pipe, the gas flow can be so controlled that in the pile or heap (11) a uniform suction pressure is achieved. In this manner the suction power can be so adjusted that more gas is withdrawn than is produced by the decomposition processes. Hitherto, suction powers were produced which were higher by a factor of about 30 than the gas formation rate measured prior to the beginning of aerobization and under anaerobic conditions. As a consequence of the air permeability of the covering (12), air flows from the surrounding into the dump and has a component thereof oxygen which passes into the heap or pile (11). This air must forcibly traverse the dump material and for that reason, apart from small amounts drawn off as samples, gas suction is locally limited to the region lying above the floor (21) of the dump, for example in the lower third of the height of the layer than this floor. By flow throughput control in each suction pipe a controlled gas exchange can be obtained over large parts of the body of the dump.

From gas samples which were taken through the filter cartridges (22) preferably in each of the wells provided or from the head of the well, gas concentrations are determined from the gas sucked up or preferably from separate multi-level wells (FIG. 2) thereby determining the gas composition and the quantity of the dump gases which arise per unit of time in terms of the spatial distribution so that any deviations from a desired optimal state can locally be evaluated and the quantity of the dump gas sucked out can be locally increased or reduced accordingly. The measurement sensors (22) or the filter cartridges thus supply the respective actual value signals for pump powers which are to be employed.

In order to optionally shift the effective suction region further downwardly, optionally a height adjustable, solid shell tube can be arranged in a suction well in a shiftable manner so that the gas withdrawal in the region of the upper gravel packing (18) can be closed off and the suction limited to the lower gravel packing (18). Whether such a shiftable tube is provided or at what height above the floor (21) of the dump the substantially single gas evacuation is to be carried out depends substantially upon the gas permeability of the heap and the maximum possible suction power as well as the type, of decomposition, which can be still anaerobic or can be aerobic. To accelerate the decomposition of the organics in the heap (11), in any case a maximum possible aerobic composition is desirable since the decomposition under these conditions is many times more rapid than with anaerobic decomposition.

Figure 2:
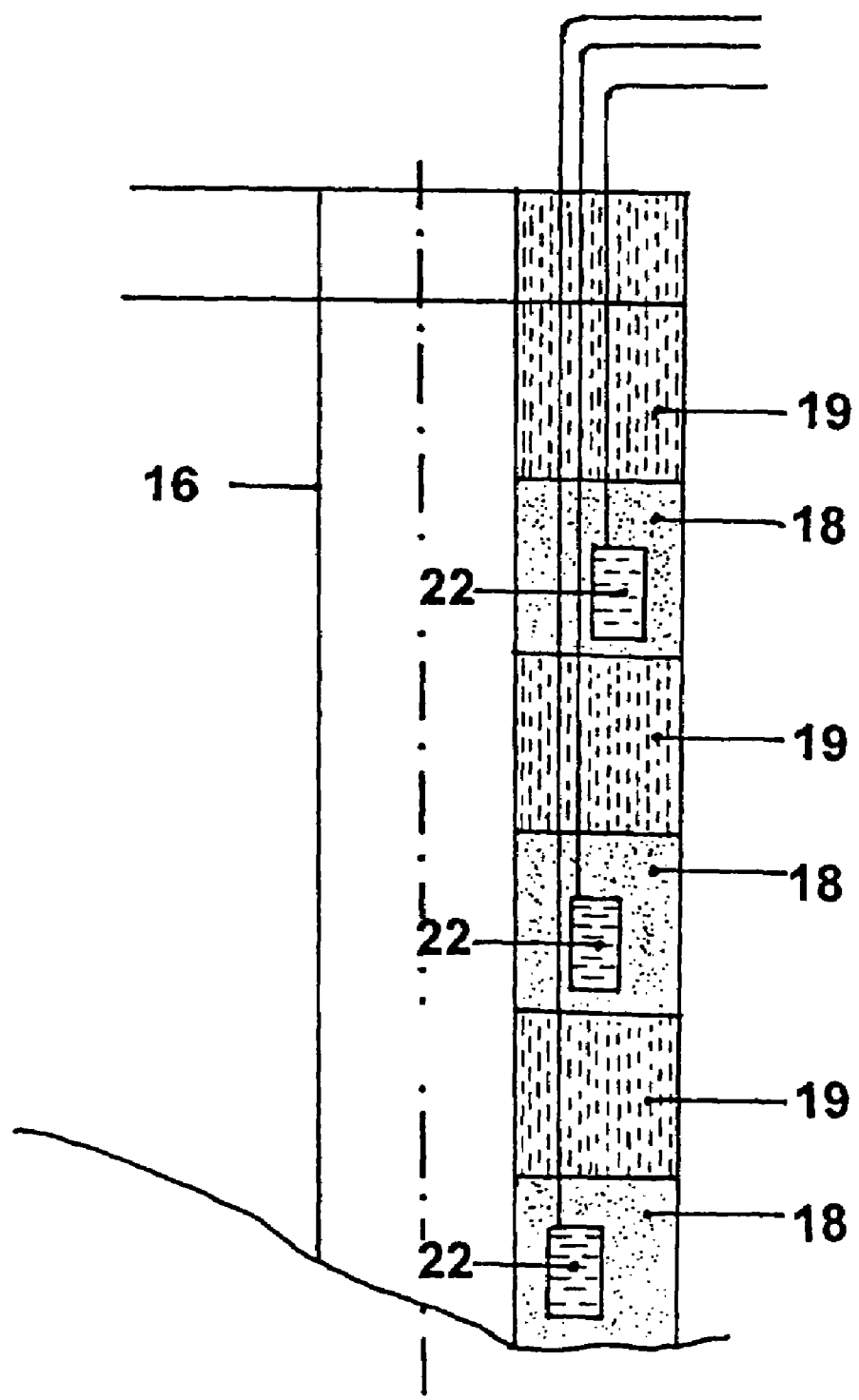

According to a further aspect of the invention, gas composition as well as the subatmospheric pressure developed in the body of the refuse dump is detected at different levels by separate multilevel wells (FIG. 2). In a bore which has not been provided with a pipe lining, layerwise, preferably respectively in one meter layers, gravel (18) and clay binder (19) are provided. In the gravel layers, during the formation thereof respective filter cartridges are introduced and are connected by measuring gas pipes to the surface. Because of the clay layers, the individual gravel layers are pneumatically separated from one another.

Via the individual measuring gas hoses, gas can be withdrawn from the individual discrete layers for analysis. Additionally the subatmospheric pressure in the individual layers can be determined. In a concrete example, the gas formation rate under anaerobic conditions were about 3 $m^3$ per hour. The methane concentration amounted about to 30 volume percent. The gas was recovered with a gas suction plant with 28 wells.

Over two newly provided gas wells with suction close to the base of the dump, initially 100 $m^3$ per hour was withdrawn. Thereafter the suction power was increased until about 500 $m^3$ per hour of gas was withdrawn. The starting $CH_4$ concentration in the withdrawn gas amounted initially to about 50 volume percent. By increasing the suction power to 400 to 500 $m^3/h$, the methane concentration in the gas withdrawn from the dump falls continuously to below 5 volume percent. In the same time the $CO_2$ content in the evacuated dump gas falls from about 25 volume percent only to 22 volume percent. Oxygen was not detectable. The total oxygen was aerobically converted to the $CO_2$. The reduction in the methane content depended upon the oversupply of the regions traversed by the drawn-in gas with atmospheric oxygen and the transformation from an anaerobic state to an aerobic and thus as reduction in methane formation and in addition to a dilution effect. The $CO_2$ concentration depended largely upon the conversion of biogenic organics with the atmospheric oxygen which was introduced.

The target of this aerobization phenomenon is the transformation from the anaerobic conversion of the organics with methane formation into a much more rapid and intensive aerobic transformation with carbon dioxide production. Critical emission paths are suppressed in that on the one hand explosion dangers with methane are reduced and on the other hand a rapid aerobic decomposition greatly reduces the carbon containing materials which are soluble in percolating water, measured as biological oxygen demand.

The described features are appropriate to buried dumps as well as for surface dumps.

The present invention also encompasses such fields of use in which, especially with dumps of considerable height, the dump has layers between layers of refuse of a binder material such as clay, loam or like substances in layers between the refuse and subdividing the dump into a plurality of horizontal regions. In such cases, each horizontal region must be treated as a separate dump. Preliminary tests have shown that gas evacuation can be carried out in each of the individual horizontal layers together with specific gas concentration measurements such that the gas evacuation can then be carried out in correspondence with the method according to the invention.

The invention claimed is:

1. A method of aerobically accelerating decomposition of $CH_4$ to $CO_2$ and $H_2O$ in garbage dumps covered by an air-permeable covering, which comprises the steps of:
    (a) depositing garbage at a garbage dump ground in a heap or pile;
    (b) suctioning out a quantity of dump gases produced by the garbage in the lower third of the pile or heap greater than the quantity of the $CH_4$ produced in the heap or pile through a plurality of suction pipes wherein said suction pipes have suction openings with upper and lower suction effective regions through which the dump gases are drawn off, arranged in the ground region of the dump, wherein the suction openings are filter stretches limited in their upper section effective regions by a gas tight shell, and only in their lower regions have one or more gas suction openings, thereby creating a vacuum at the bottom of the dump to provide suction;
    (c) following step (b), suctioning into the lower third of the heap or pile oxygen in atmospheric air through an exterior surface of the air-permeable covering of the dump or pile so that oxygen forcibly traverses the heap or pile and penetrates downwardly into the heap or pile resulting in an oxygen excess; and
    (d) directly and uniformly aerating the entire heap or pile with the oxygen excess sucked into the lower third of the heap or pile, to limit $CH_4$ formation from the garbage while effecting an aerobic decomposition of the $CH_4$ to $CO_2$ and $H_2O$, thereby transforming an anaerobic decomposition process into a decomposition which is at least mostly an aerobic decomposition.

2. The method according to claim 1, wherein according to step (b) the suctioning out of the dump gases is conducted exclusively in the region of the dump ground and/or in a zone which extends to 6 meters above the dump ground.

3. The method according to claim 1, wherein according to step (b) the suctioning out of the gas is carried out at a multiplicity of locations arranged in the region of the dump ground.

4. The method according to claim 1, wherein according to step (b) the suction power is so controlled in dependence upon the gas composition measured at different heights in the pile or heap that each location in the pile or heap an oxygen content is established as is required for an aerobic decomposition.

5. The method according to claim 1 wherein according to step (b) the suctioning out of the dump gases is carried out at multiple locations arranged in the region of the dump ground and which are equidistant from one another.

6. An apparatus for aerobically accelerating decomposition of $CH_4$ to $CO_2$ and $H_2O$ in a garbage dump in a heap or pile covered by an air-permeable covering, which comprises:
    (a) a plurality of suction pipes included in the heap or pile and extending to the ground region of the garbage dump for suctioning off dump gases from the lower third of the heap or pile, wherein each suction pipe has suction openings with upper and lower suction effective regions arranged in the ground region of the dump, wherein the suction openings are filter stretches limited in their upper suction effective regions by a gas tight shell so that only the filter stretches in the lower suction effective regions have one or more gas suction openings;
    (b) at least one measurement sensor for analyzing and measuring concentration of dump gases comprising $CH_4$ arising in the heap or pile;
    (c) a control device for adjusting a throughflow quantity of the dump gases drawn off from the plurality of suction pipes as detected by the measurement sensor; and
    (d) means for providing suction at the bottom of the heap or pile of the garbage dump for the plurality of suction pipes for suctioning off dump gases and for forcibly introducing flow of oxygen in atmospheric air through an exterior surface of the air-permeable covering of the heap or pile to the bottom of the heap or pile, to directly traverse the heap or pile, providing uniform aeration of the entire heap or pile resulting in an oxygen excess, to effect an aerobic conversion of the $CH_4$ to $CO_2$.

7. The apparatus according to claim 6 wherein a plurality of suction pipes are installed whose positions, spacing and pump capacity are so selected that their respective suction effective regions at least bound one another.

8. The apparatus according to claim 7 wherein the pump power in each suction pipe is individually controllable.

9. The apparatus according to claim 6, wherein the suction extends to below the ground water level.

10. The apparatus defined in claim 6 wherein the suction openings of the suction pipes are arranged in the lower third of the dump pile or heap and/or in a region which extends through a maximum of 6 meters above the dump or heap floor from the dump or heap floor.

11. The apparatus defined in claim 6 wherein the plurality of suction devices incorporated in the heap or pile are mutually equidistantly arranged.

12. The apparatus defined in claim 6 wherein the positioning, spacing and pump capacity of the plurality of suction pipes are so arranged that their respective suction effective regions overlap one another.

13. The apparatus defined in claim 6 wherein the pump power in each suction pipe is individually controlled dependent upon the gas concentration measured in the respective effective region.

* * * * *